(12) United States Patent
Hack

(10) Patent No.: US 7,942,876 B2
(45) Date of Patent: May 17, 2011

(54) INTRA-MEDULLARY IMPLANT WITH ACTIVE COMPRESSION

(75) Inventor: Bradford H. Hack, La Canada, CA (US)

(73) Assignee: Accelerated Orthopedic Repair, LLC, Reno, NV (US)

( * ) Notice: Subject to any disclaimer, the term of this patent is extended or adjusted under 35 U.S.C. 154(b) by 1176 days.

(21) Appl. No.: 11/372,853

(22) Filed: Mar. 10, 2006

(65) Prior Publication Data

US 2007/0213725 A1 Sep. 13, 2007

(51) Int. Cl.
*A61F 2/30* (2006.01)

(52) U.S. Cl. ........................................ 606/64; 606/62

(58) Field of Classification Search ............. 606/63, 606/64, 65, 66, 67, 68, 62, 300, 301, 302, 606/303, 304, 305, 306, 307, 308, 309, 310, 606/311, 312, 313, 314, 315, 316, 317, 318, 606/319, 320, 321, 322, 323, 324, 325, 326, 606/327, 328, 329, 330, 74–75
See application file for complete search history.

(56) References Cited

U.S. PATENT DOCUMENTS

| 3,441,017 | A | * | 4/1969 | Kaessmann | 606/64 |
|---|---|---|---|---|---|
| 4,190,044 | A | * | 2/1980 | Wood | 606/63 |
| 5,263,955 | A | * | 11/1993 | Baumgart et al. | 606/63 |
| 5,318,575 | A | * | 6/1994 | Chesterfield et al. | 606/151 |
| 5,766,180 | A | * | 6/1998 | Winquist | 606/104 |
| 6,589,246 | B1 | * | 7/2003 | Hack et al. | 606/74 |
| 2004/0127907 | A1 | * | 7/2004 | Dakin et al. | 606/72 |

* cited by examiner

*Primary Examiner* — Eduardo C Robert
*Assistant Examiner* — Jan Christopher Merene
(74) *Attorney, Agent, or Firm* — Laura Tunnell

(57) ABSTRACT

An Intra-Medullary implant includes: an elongated rigid body having a first end and a second end, adapted to be inserted longitudinally into a bony canal, the body having a generally axial passage through at least a portion of said body; at least one movable slide, movably received in said passage and adapted to be transfixed by engagement with a transverse member penetrated through the bone, said slide also adapted to receive tension from an elongated tensile member disposed longitudinally within said passage; and an anchor, adapted for fixation to the body near its first end and to said tensile member, to hold the elongated tensile member under tension between the anchor and the movable slide.

13 Claims, 2 Drawing Sheets

INTRA-MEDULLARY IMPLANT WITH ACTIVE COMPRESSION

BACKGROUND OF THE INVENTION

1. Field of the Invention

This invention relates to surgical devices generally and more specifically to orthopedic implants for stabilizing fractured bones, especially a human femur.

2. Description of the Related Art

Intramedullary rods (sometimes called "nails"), usually of a steel or titanium alloy, are used in orthopedic surgery to aid in the fixation of long bone fractures. The originator of the Intramedullary rod implant was a German surgeon called Kuntscher; for this reason the original implant was sometimes called a "Kuntscher nail." Eventually Kuntscher's nailing technique, became a common orthopedic procedure, especially for fractured femurs or Tibias.

Modern orthopedic practice is slightly different from that used by Kuntscher, and is referred to as "Closed nailing." To fix a fracture with an intramedullary rod, the fracture is first reduced. Then a small hole is made usually at the top of the bone (antegrade placement). A reamer is typically used to prepare the intramedullary canal to snugly receive a rod-like implant. Usually a thin guide wire is slid down inside the bone, across the fracture and into the next fragment. A long rod is then inserted longitudinally and generally axially into the intramedullary canal, the rod spanning the unstable, fractured area. Often, interlocking screws are inserted generally diametrically through holes drilled in the intact sections of the bone, both above and below the fracture. The interlocking screws pass through the bone and through transverse holes in the intra-medullary rod, thereby transfixing the bone to the inserted rod and longitudinally and torsionally stabilizing the fracture.

Depending on the innate stability of the fracture, the screws may be essentially static and provide rigid, inflexible fixation of the bone without significant compression. If the fracture is longitudinally stable, the interlocking screws can be threaded through elongated holes or slots in the intra-medullary rod, thus allowing the fractured bone ends to be pressed together somewhat. This method allows some limited compression, due to gravity or (in some cases) muscular contraction; but compression only occurs sporadically, if weight bearing can be tolerated.

Research has shown that a more sustained, controlled, and dynamic compression across a fracture is desirable to promote rapid healing. Furthermore, it is known that in many fractures, bone resorption typically precedes mending. A rigid intra-medullary rod cannot accept any degree of bony contraction.

SUMMARY OF THE INVENTION

In view of the above problems, the present invention provides an orthopedic implant for aiding in fixation of a fracture in a long bone, suitable for intra-medullary implantation. The implant includes: an elongated rigid body having a first end and a second end, adapted to be inserted longitudinally into a bony canal, the body having a generally axial passage through at least a portion of said body; at least one movable slide, movably received in said passage and adapted to be transfixed by engagement with a transverse member penetrated through the bone, said slide also adapted to receive tension from an elongated tensile member disposed longitudinally within said passage; and an anchor, adapted for fixation to the body near its first end and to said tensile member, to hold the elongated tensile member under tension between the anchor and the movable slide.

According to another aspect, the invention also provides a method for fixing a fracture in a long bone to promote healing. The method includes the steps of: a) inserting a generally hollow, elongated implant having a first end and a second end in the intra-medullary canal of the bone with said implant crossing the fracture, to stabilize the fracture; b) transfixing a slidable device inserted in said implant below the fracture, by cross nailing said device transversely to the bone below the fracture; c) fixing said first end to the bone above the fracture; d) applying elastic tension between the first end of the implant and the transfixed slide; and e) maintaining said tension in a predetermined range for a time sufficient to promote healing of the bone.

According to yet another aspect, the invention provides an orthopedic implant for aiding in fixation of a fracture in a long bone, suitable for intra-medullary implantation. The implant includes: a substantially rigid elongated body, adapted for insertion into a bony canal to stabilize the fracture; a movable member slidably retained by said elongated body and arranged to be transfixed to the long bone; a tensioning mechanism coupled to said movable member and said elongated body, arranged to apply compression across the fracture to promote healing.

These and other features and advantages of the invention will be apparent to those skilled in the art from the following detailed description of preferred embodiments, taken together with the accompanying drawings, in which:

DETAILED DESCRIPTION OF THE INVENTION

The invention includes an apparatus and method for applying a consistent predetermined elastic force longitudinally across a fracture in (typically generally cylindrical) bone. The compressive force is generated by at least one elastomeric tensile member included in the intra-medullary implant, together with transfixing cross-pins that engage the bony fragments on both sides of the fracture under tension, tending to draw the bony fragments inward toward one another in a geometry stabilized by the intra-medullary implant.

Figure 1:
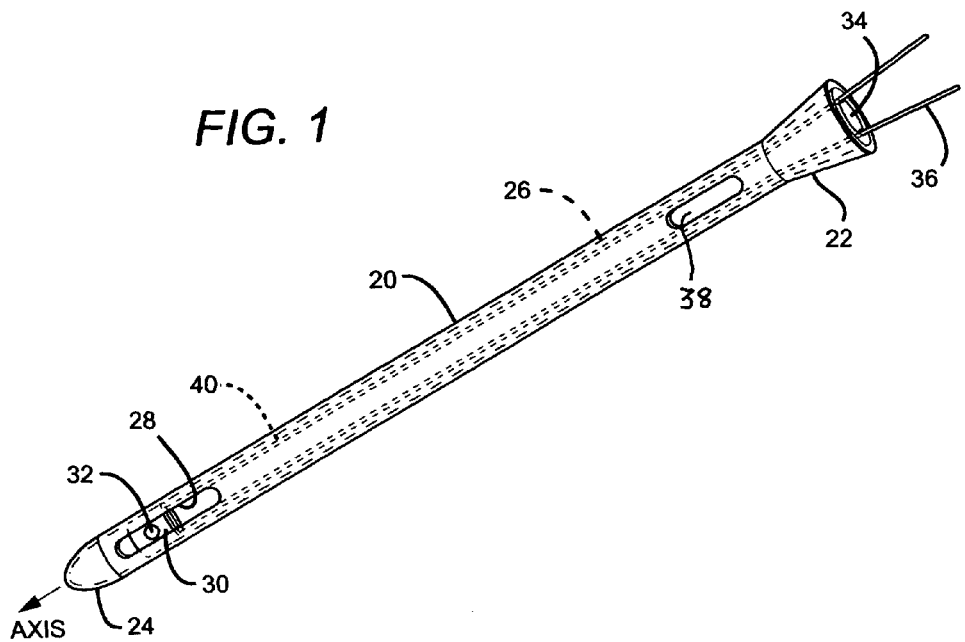
FIG. 1 is a perspective view of an intra-medullary implant in accordance with the invention.

FIG. 1 shows an intra-medullary implant, specifically a rod, in accordance with the invention. The specific example shown is suitable for implantation in a human femur, and is characteristically straight. The invention is not limited to this specific geometry, but the embodiment shown is particularly useful to aid in fixation of fractured femoral necks. For example, in another embodiment, suitable for fixing a human tibia, a slight angulation or "dog-leg" may be provided, without departing from the invention.

The apparatus of the invention will be described, in some aspects, in relation to a presumed placement in a fractured bone. Where reference is made to "proximal" and "distal" below, an antegrade insertion is presumed; it will be apparent to one skilled in the art to re-orient the directions if a retrograde insertion is to be employed.

The generally elongated body (member) 20 has a proximal end 22 and a distal end 24, disposed at opposite ends of the body. An internal channel 26 (shown in broken lines) extends generally axially through a substantial longitudinal portion of the body 20 (better seen in sectional views discussed below). Near the distal end 24 of the body 20 a slot or port 28 opens to expose a portion of a slide 30, received slidably within the channel 26. A through hole 32 is provided in slide 30, to allow the slide to be transfixed by the transverse insertion of a pin or screw inserted transversely through a bone, as further discussed below.

At the proximal end 22 of the body 20, a plug or other anchor 34 is provided. In the example shown, the anchor 34 is a tapered plug, generally shaped like a frustrum (specifically, a conical frustrum) having cable retention groove or grooves. At least one free end of cable 36 can be seen extending from the anchor 34.

In the embodiment shown, the proximal end 22 is shouldered or tapered in the manner of a cork or countersink. This configuration offers one method of fixing the proximal end with respect to the proximal portion of the bone (on the proximal side of the fracture). In other words, the proximal end wedges into a taper or constraint in the (prepared) bone canal, preventing the implant from translating further into the canal. Alternatively, the proximal end 22 of the pin could be transfixed by passing a pin or screw through a slot or hole 38, disposed near the proximal end, as in many conventional, static IM rods. The distal end of the rod is arranged to be transfixed by a pin or screw piercing transversely across the distal portion of the bone (below the fracture), fixing the distal bone portion in relation to the slide. A tensile member 40 urges the slide and the anchor inwards toward one another, and thus urge the bone components in turn toward one another (providing compression across the fracture).

Although the anchor plug 34 as shown in the figures is advantageous, and forms an important feature of one specific embodiment, other anchors could be used in variants of the invention to adapt to different orthopedic applications as required. Furthermore, the figure shows two free ends 36 of a cable extending from the proximal end of the body; the number of cable strands or the method of anchoring these strands can be varied according to the specific implant requirements.

Figure 2:
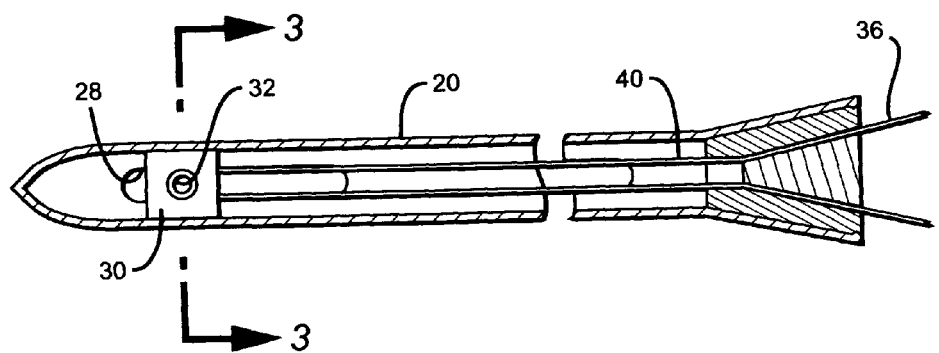
FIG. 2 is a sectional view taken along a longitudinal section including the axis of the implant of FIG. 1.

FIG. 2 shows the body 20 with a substantial section cut away, exposing the internal structures to view. One can see at least one internal elastomeric tensile member 40 (typically a polymer cable) extending between the anchor 34 and the slide 30. In the embodiment shown, a single cable provides two tensile members by doubling the cable over the slide in the manner of a pulley. A single cable or a plurality of cables could be used in variants, to provide more or less tension consistent with the therapeutic needs of the implant site. The doubled cable arrangement shown in the figures is advantageous because it allows easy tensioning of the cable working from the free end (at the proximal end of the body). However, other arrangements are possible.

Besides an engineered polymer cable (discussed below), other materials could be used in some embodiments; but an engineered polymer cable having unusual properties is greatly preferred.

Figure 3:
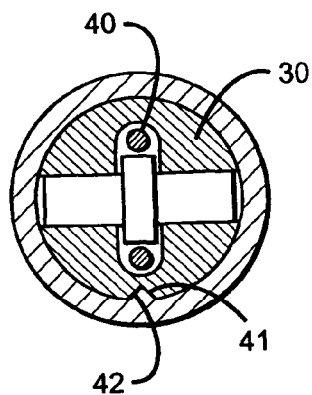
FIG. 3 is a cross sectional view taken along section 3 shown in FIG. 2.

FIG. 3 shows the body in a cross section intersecting the included slide 30. A slot 41 can be seen in the slide, which slidably engages with a complementary longitudinal rail 42 in the interior of the body 20. This arrangement prevents the slide from twisting, which in turn maintains the slide in a position to be easily transfixed by pinning through the bone, as discussed below. Other methods could be used to prevent rotation of the slide 30. For example, a non-cylindrical channel and complementary slide could be used.

Figure 4:
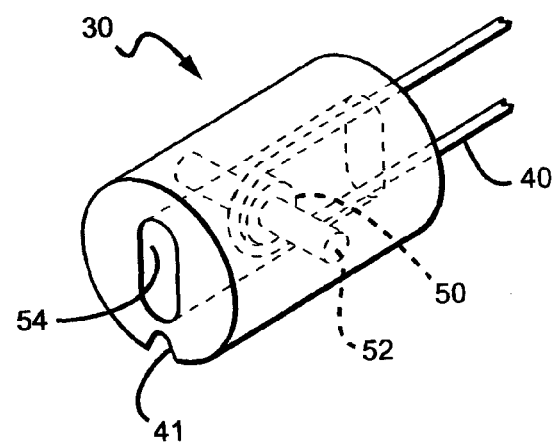
FIG. 4 is a perspective view of the slide in FIG. 2, in relation to an elastomeric tensile member in one suitable configuration.

FIG. 4 shows the slide 30 removed from the elongated body, and in relation to the tensile member 40. In one embodiment the slide has a transverse hole 48 (or slot) including a generally cylindrical bushing 50. The tensile member 40 is looped over the bushing, thereby engaging the slide. The transverse bushing 50 includes and defines a transverse channel 52 that is adapted to engage with transfixing cross pins or screws passed transversely through the bone, in a manner similar to that used to fix traditional intramedullary rods.

Figure 5:
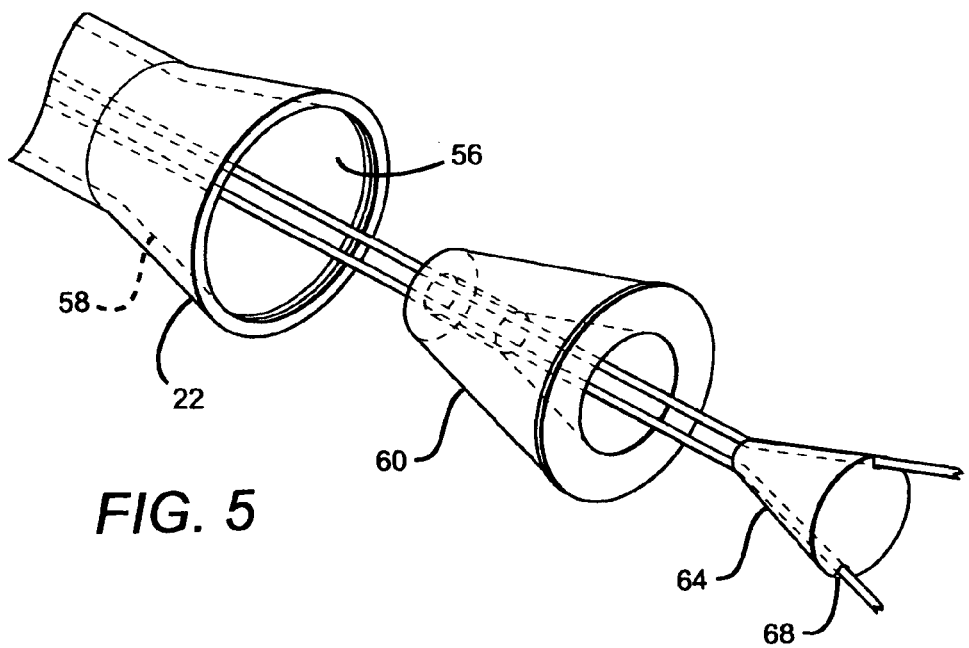
FIG. 5 is an exploded view of a cable retention device or anchor, suitable for retaining a cable under tension in the intra-medullary implant of FIGS. 1-4.

The proximal end of the intra-medullary implant is shown in exploded detail in FIG. 5. The mechanism shown provides a suitable way of securing a tensioned cable (tensile member 40) previously looped over the slide. The proximal end of the body 20 is flared as shown, tapering in the manner of a countersink, generally conically from a wider proximal mouth 56 to a narrower lower throat 58. A rigid outer swage member 60, externally resembling a conical frustrum, fits into the mouth 56 and lodges due to the constrained tapered throat. The swage member 60 also has a tapered, generally conical recess 62 therein, which in turn is adapted to receive a tapered plug 64 with a generally conical taper, snugly fitting the conical recess 62. At least one of the swage member 60 and the plug 64 preferably have at least one groove 68 or gutter-like channel running generally longitudinally to engage and compress the tensile member (cable) 40. The groove or grooves are disposed in relation to the taper so that any contraction of the tensile member tends to draw the plug 64 further downward in the direction of the tension, wedging the plug more tightly and gripping the cable with increasing tension. This arrangement facilitates setting the cable under a desired, predetermined tension; thereafter the tension causes the plug 64 to retain the cable ends without slipping, secured by the wedge action of the tapered plug seated in the generally conical recess 62 in the swage member 60.

Optionally, internal or external threads may be provided near the top of the IM rod. A tool with complementary threads can suitably be screwed onto the top of the device to compress the plug 64 and swage into the body, compressing and securing the cable due to the taper of the plug 64.

More details of a mechanism for securing the cable under tension are given in U.S. patent application Ser. No. 11/147,685.

The method of using the invention will next be described.

The fractured bone is first prepared in accordance with proper surgical practice. An implant as shown of FIGS. 1-5 is then provided, preferably in a sterilized and hermetically sealed package convenient for the surgical environment. Preferably the implant has been partially assembled, with the tensile member engaging the slide 30 but without any tension established. If not, the surgeon or support personnel would assemble the implant at this time.

The surgeon inserts the implant longitudinally into the intra-medullary canal, disposing the implant so that the port 41 and slide are positioned well below the fracture site, with the proximal end of the implant extending well above the fracture. The implant should fit the canal sufficiently to stabilize the bone across the fracture into a substantially linear, cylindrical structure.

Next a transverse hole is drilled through the bone below the fracture, for a bone screw or pin to transfix the slide 30. Various methods of locating the port or slide could be used, including imaging or various non-imaging measuring procedures. One method is described in U.S. Pat. No. 6,027,506, for example. Other methods are described in trade publications, available for example from Stryker Corporation and other manufacturers of orthopedic surgical devices.

After the transverse hole is drilled, a transfixing screw or pin is threaded through the bone, skewering and engaging the slide 30 by passing through the transverse channel through said slide. After The slide is secured, the fracture should be compressed into desired position pushing the flared proximal end downward while drawing the cable upward in opposition to one another, while providing any necessary rotation or manipulation to guide the fracture to a desired position.

When the fracture has been brought to the desired position, the surgeon will draw a desired tension on the cable, while simultaneous firmly seating the wedge-like plug 64 to retain the cable tension. The excess cable can be removed slightly behind the plug, leaving a few millimeters of excess for safe retention. In this configuration the tension will tend to compress the fracture dynamically while the linear, rod like geometry of the implant stabilizes the fracture against bending or shearing displacement.

It has been found that strains in the range of 1500 to 4000 microstrains are desirable to promote healing in bony fractures. Accordingly, in one embodiment of the invention the tensile member provides such strain by applying force in the range 18 to 100 lbs-force or approximately 80-450 Newtons. Similarly, a preferred embodiment of the method includes the action of applying a tension in the range 18 to 100 lbs-force or 80-450 Newtons. Furthermore, it is greatly preferred that the tension be maintained in the preferred range for an extended period, sufficient for considerably healing of the bone to occur. Therefore, the method should include maintaining the tension in said range for a period sufficient for substantial healing to occur.

Tension can be set by drawing the cable with a calibrated tool, thereby controlling the applied tension.

A cable suitable for use as tensile member 40 in the invention should have at least two qualities: a) relatively high breaking strength, in the range at least 200 and preferably 400 lbs for a cable of 1-2 mm in diameter, and b) the ability to maintain the tension within a desired range notwithstanding substantial displacement (plus or minus) of the fracture. It is known that fractures may slightly contract due to resorption prior to healing, which may create shortening of the bone of up to of several millimeters. It is also known that living bone under changing loads flexes, extending and contracting in response to load. For this reason, to maintain proper compression on the fracture the tensile member of the invention should preferably possess specific force/extension characteristics at the working tension (in the 80-450 Newton range). We can define an axial modulus parameter Q as the cable tension (in Newton's) multiplied by the cable's static (unloaded) length, divided by the quantity working length minus unloaded length. For preferred embodiment, this axial modulus Q should preferably be below 1400 (Newtons), and more preferably in the Range of 160 to 1800 Newton's. Higher values impose difficulties in accurately imposing and maintaining tension, based on the precision of the assumed cable take-up mechanism. In other words, Q values below 1800 are preferred so that the working elongation is a manageable displacement at the working tension Preferably, the cable's force/extension characteristic should preferably be relatively linear in the working region. Weaker elastomeric cables (such as urethane monofilament) are capable of significant contraction/extension while maintaining substantially constant tension; but such cables are not suitable because they exert insufficient working tension. On the other hand, metal alloy cables exert significant tension but do not maintain the working tension within a zone of tolerance if stretched or slackened by millimeters. Metal cables cannot stretch over the load ranges required, primarily because of their high elastic modulus.

The strength and extension characteristics discussed above should also be understood in the context of working lengths and diameters suitable for use in an IM rod.

Typical cable diameters for this application would be in the 1.0-2.0 millimeter range; working lengths are typically in the 10-30 cm range, constrained by the length of the rod.

Suitable cable preferably should also allow substantial elongation without danger of failure. For this reason the cable should preferably be capable of extension by a substantial percentage, preferably 50 and more preferably at least 100 percent, without significant risk of failure. Furthermore, it will be apparent that bio-compatible materials should be employed, more specifically, bio-compatible materials that can be suitably sterilized and preferably packaged in hermetically sealed packaging for distribution.

While several illustrative embodiments of the invention have been shown and described, numerous variations and alternate embodiments will occur to those skilled in the art. For example, other means of gripping the elastic member could be employed, including but not limited to wedges, posts, and screws. Such variations and alternate embodiments are contemplated, and can be made without departing from the spirit and scope of the invention as defined in the appended claims.

I claim:

1. An orthopedic implant for aiding in fixation of a fracture in a long bone, suitable for intramedullary implantation, comprising:
    an elongated rigid body having a first end and a second end, adapted to be inserted longitudinally into a bony canal, said body having a generally axial passage through at least a portion of said body;
    at least one movable slide, movably received in said passage and adapted to be transfixed by engagement with a transverse member, wherein said transverse member is operable for penetration through a bone, said slide also adapted to receive tension from an elastomeric tensile member, said elastomeric tensile member having a first end and a second end, and wherein said elastomeric tensile member is disposed longitudinally within said passage and looped around said slide;
    an anchor adapted to engage said body near said first end, operable for holding said first and said second end of said elastomeric tensile member under tension between said anchor and said movable slide, said anchor being comprised of an outer swage member, an inner mated plug, and two longitudinal grooves therebetween,
    wherein said outer swage member is a conical frustum, said conical frustum having an axis that is colinear with said axial passage of said elongated body,
    wherein said inner mated plug is also conical in shape, said conical shape also having an axis that is colinear with said axial passage of said elongated body,
    and wherein said longitudinal grooves are operable for compressing said first end and said second end of said elastomeric tensile member between said outer swage member and said inner swage member.

2. The implant of claim 1 wherein said elastomeric tensile member comprises a cable, said cable having at least one elastic polymer core fiber enveloped by a high strength polymer jacket.

3. The implant of claim 2 wherein said jacket comprises a woven plurality of ultra-high molecular weight, polyethylene fibers.

4. The implant of claim 2 wherein said cable has an axial modulus in the range of 160 to 1800 Newtons.

5. The implant of claim 4 wherein said cable is capable of elongation by at least 30 per cent over its unstressed length without failure.

6. The implant of claim 1 wherein said first end of said body has a tapered shoulder for seating in a countersunk bony recess.

7. The implant of claim 1 wherein said elastomeric tensile member is adapted to sustain a working tension in the 80-450 Newton range, with elongation in the 30 to 150 per cent range.

8. The implant of claim 1 wherein said body has a slot disposed generally toward the second end of said body, said slot arranged to expose at least a portion of said slide for transverse fixation to the long bone.

9. The implant of claim 1 wherein said slide includes a pulley adapted to receive said elastomeric tensile member.

10. A method of fixing a fracture in a long bone to promote healing, comprising the steps:
- inserting a generally hollow, rigid, elongated implant having a first end, a second end, and a generally axial passage through at least a portion of said implant in the intramedullary canal of the bone with said implant crossing the fracture, to stabilize the fracture;
- transfixing a slidable device inserted in said implant below the fracture, by cross nailing said device transversely to the bone below the fracture, wherein said slidable device is movably received in said passage and adapted to be transfixed by engagement with a transverse member, wherein said transverse member is operable for penetration through a bone, said slide also adapted to receive tension from an elastomeric tensile member, said elastomeric tensile member having a first end and a second end, and wherein said elastomeric tensile member is disposed longitudinally within said passage and looped around said slide;
- fixing said first end to the bone above the fracture;
- applying elastic tension between the first end of the implant and said transfixed slide via an anchor engaging said implant near said first end, operable for holding said first and said second end of said elastomeric tensile member under tension between said anchor and said movable slide, said anchor being comprised of an outer swage member, an inner mated plug, and two longitudinal grooves therebetween,
- wherein said outer swage member is a conical frustum, said conical frustum having an axis that is colinear with said axial passage of said elongated implant,
- wherein said inner mated plug is also conical in shape, said conical shape also having an axis that is colinear with said axial passage of said elongated implant,
- and wherein said longitudinal grooves are operable for compressing said first end and said second end of said elastomeric tensile member between said outer swage member and said inner swage member; and
- maintaining said tension in a predetermined range for a time sufficient to promote healing of the bone.

11. The method of claim 10, wherein said elastic tension is maintained in the range from 80-450 Newtons, inclusive.

12. The method of claim 11, wherein said elastic tension is maintained by said elastomeric tensile device, said elastomeric tensile device including an elastomeric cable with an axial modulus in the 160-1800 Newton range, where axial modulus is defined as the working tension times the unloaded length, divided by the quantity loaded length minus unloaded length.

13. The method of claim 10, wherein said step of applying tension comprises stretching said elastomeric tensile device in tension between said first end and said slide, said elastomeric tensile device within said axial passage of said generally hollow elongated implant.

* * * * *